(12) United States Patent
Kanemaru et al.

(10) Patent No.: US 7,449,193 B2
(45) Date of Patent: Nov. 11, 2008

(54) SILICONE-TREATED POWDER, PROCESS OF PRODUCTION THEREOF AND COMPOSITION CONTAINING THE SAME

(75) Inventors: Tetsuya Kanemaru, Yokohama (JP); Kyoko Jouichi, Yokohama (JP); Kazuhisa Ohno, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 64 days.

(21) Appl. No.: 10/679,298

(22) Filed: Oct. 7, 2003

(65) Prior Publication Data

US 2004/0047887 A1 Mar. 11, 2004

Related U.S. Application Data

(63) Continuation of application No. 09/753,569, filed on Jan. 4, 2001, now abandoned.

(30) Foreign Application Priority Data

Jan. 14, 2000 (JP) ................................ 2000-10146

(51) Int. Cl.
*A61K 8/02* (2006.01)
(52) U.S. Cl. ..................................................... 424/401
(58) Field of Classification Search ................. 424/401, 424/489
See application file for complete search history.

(56) References Cited

U.S. PATENT DOCUMENTS

| | | | | |
|---|---|---|---|---|
| 4,578,266 A | | 3/1986 | Tietjen et al. | |
| 4,876,039 A | * | 10/1989 | Lo et al. | ....................... 264/4.7 |
| 5,118,496 A | | 6/1992 | Herstein | |
| 5,130,171 A | * | 7/1992 | Prud'Homme et al. | . 427/213.36 |
| 5,548,054 A | | 8/1996 | Okada et al. | |
| 5,635,250 A | * | 6/1997 | Blum et al. | .................. 427/387 |
| 5,650,004 A | | 7/1997 | Yon | |
| 2002/0142094 A1 | * | 10/2002 | Fukushima et al. | ......... 427/214 |

FOREIGN PATENT DOCUMENTS

| | | |
|---|---|---|
| EP | 0 212 870 A | 3/1987 |
| EP | 0 522 916 A2 | 1/1993 |
| FR | 2 186 221 | 1/1974 |
| JP | 06 016971 A | 1/1994 |
| JP | 092484 * | 4/1996 |
| JP | 09-053023 A | 2/1997 |
| JP | 09-268271 * | 10/1997 |
| JP | 11-209646 A | 8/1999 |

* cited by examiner

*Primary Examiner*—M P Woodward
*Assistant Examiner*—Bethany Barham
(74) *Attorney, Agent, or Firm*—Foley & Lardner LLP

(57) ABSTRACT

A silicone-treated powder composed of a powder coated on the surface thereof with a silicone compound, wherein an amount of hydrogen generated by Si—H groups remained on the surface of the silicone-treated powder is not more than 0.2 ml/g of treated powder and a contact angle of water with the treated powder is at least 100°.

8 Claims, No Drawings

SILICONE-TREATED POWDER, PROCESS OF PRODUCTION THEREOF AND COMPOSITION CONTAINING THE SAME

BACKGROUND OF THE INVENTION

1. Field of the Invention

The present invention relates to a process for producing a silicone-treated powder, more specifically relates to a silicone-treated powder obtained by coating a silicone compound having an Si—H group on the surface thereof and polymerizing the silicone on the surface thereof by heat treatment to obtain water repellency and to eliminate almost all the residual Si—H groups on the coating, to thereby be able to be formulated into various cosmetics, and superior in stability in a product, and a production process thereof.

2. Description of the Related Art

There have been various methods for giving hydrophobicity to a powder in the past. Using the hydrophobicity of silicone oil is well known.

The silicone compounds usable for providing hydrophobicity are those having an organohydrogenpolysiloxane chain in the molecule and also sometimes having a diorganopolysiloxane chain in the molecule or a mixture of organohydrogenpolysiloxane and diorganopolysiloxane. When these compounds are coated on the surface of a powder, the Si—H group bonded portion of the organohydrogenpolysiloxane molecule reacts with the moisture etc. in the air due to the surface activity of the powder, and the Si—OH groups produced react with the Si—H groups of the other adjacent molecules, or the Si—OH groups react among themselves to cause cross-linking and polymerization and to form a silicone film.

However, with heat treatment in the air at about 200° C. after coating organohydrogenpolysiloxane on the surface of a powder, the residual Si—H groups are not completely eliminated, while the cross-linking reaction of the molecules themselves proceeds to a certain extent. On the other hand, with heating at 500° C. or more, the silicone starts to burn and is converted to silica (see Japanese Unexamined Patent Publication (Kokai) No. 11-199458, the treatment for coating silicon oxide by heating at a temperature of 600 to 950° C.

The residual Si—H groups react with the moisture in the air or the moisture, alcohol, amines, etc. in makeup products over a long period of time to cause the production of hydrogen and form new siloxane bonds, and therefore, if the above treated powder is used as it is for cosmetics, coating compositions, toners, inks, containers, and ingredients of various other compositions, various problems will sometimes be caused in the compositions.

For example, in the case of cosmetics, there is a risk of generation of hydrogen in the production process, the containers may swell with the elapse of time after filling the product into containers, and the product may harden and crack. In the case of coating compositions, the problem of deterioration of the container sometimes occurs.

To reduce the above-mentioned residual Si—H groups, for example, the method of Japanese Unexamined Patent Publication (Kokai) No. 63-113081 (i.e., Japanese Patent No. 1635593) (i.e., the addition of a compound having unsaturated hydrocarbon group to residual Si—H groups by hydrosilylation reaction), the method of Japanese Unexamined Patent Publication (Kokai) No. 8-192101 (i.e., the substitution of residual Si—H groups by contact with water or lower alcohol), the method of Japanese Examined Patent Publication (Kokoku) No. 56-43264 (i.e., the mixture and pulverization of metal hydroxide serving as a catalyst for cross-linking and polymerization of organohydrogenpolysiloxane with a treated powder, then using mechanochemical reaction), etc. have been attempted.

The above methods are effective in their own right, but the processes are complicated, a long time is required, or relatively active functional groups are adsorbed on the surface, and therefore the powder is given an unpleasant smell etc.

SUMMARY OF THE INVENTION

In view of the above-mentioned situation, the object of the present invention is to provide a silicone-treated powder free from generation of hydrogen and having a good quality and also a process for producing such a silicone-treated powder and a process of production having a reduced manufacturing cost.

That is, according to the present invention, there is provided a silicone-treated powder comprising a powder coated on the surface thereof with a silicone compound wherein an amount of hydrogen generated by Si—H groups remained on the surface of the silicone-treated powder is not more than 0.2 ml/g of treated powder and a contact angle of water with the treated powder is at least 100°.

In accordance with the present invention, there is also provided a process for producing a silicone-treated powder comprising the steps of:

coating a surface of a powder with
  (1) a silicone compound having at least one Si—H group or
  (2) a mixture of the silicone compound (1) and a silicone compound not having an Si—H group and; then
heating the silicone compound coated powder at a temperature of 260 to 480° C. for 0.1 to 24 hours.

Here, when the average particle size of the powder is not more than 0.1 μm, the silicone compound coated powder is preferably heated in the second step at 260 to 350° C. for 1 to 5 hours, while when the average particle size of the powder is not less than 0.1 μm, the silicone compound coated powder is-preferably heated in the second step at 330 to 480° C. for 1 to 5 hours.

In accordance with the present invention, there are further provided a cosmetic composition comprising the above silicone-treated powder, as one ingredient of the formulating material and a carrier thereof, a coating composition comprising the above silicone-treated powder as one ingredient of the formulating material and a carrier thereof, and a resin molded article obtained by injection molding a synthetic resin composition containing the silicone-treated powder as one ingredient of the formulating material. Here, the cosmetic composition preferably includes a solid foundation, emulsion foundation, pressed powder, face powder, UV blocking stick, lipstick, water-in-oil type emulsion sunscreen, and body powder.

DESCRIPTION OF THE PREFERRED EMBODIMENT

The present invention will now be explained in more detail. In this specification and in the claims the singular forms "a", "an" and "the" include plural referents unless the context clearly dictates otherwise.

The present inventors engaged in intensive research and, as a result, found that by heating a powder coated with organohydrogenpolysiloxane etc. at a temperature of 260 to 480° C., it is possible to cross-link or substitute with inert functional groups almost all of the residual Si—H groups while maintaining the hydrophobicity, whereby the present invention was completed.

The powder usable in the present invention is not particularly limited, but includes, for example, an organic pigment, inorganic pigment, metal oxide, metal hydroxide, mica, pearl agent, metal, magnetic powder, silicate ore, resin powder, powder having rubber elasticity, or a porous substance alone or in any combination thereof.

Particularly preferable powders among these are any inorganic powders having particle sizes of not more than 1 mm (sometimes including particles larger than 1 mm). Specifically, metal oxides, metal hydroxides, clay minerals, pearl agents, metals, carbon, magnetic powder, silicate ores, porous materials, etc. are exemplified.

These powders may be used alone or in any combination thereof. Further, they may be in a coagulated mass or in the form of a molded or shaped article. According to the present invention, it is possible to modify (or treat) any inorganic powder including even superfine powder having a particle size of not more than 0.02 μm.

Here, specific examples of the inorganic pigments (including metal oxides and metal hydroxides), include, for example, Prussian Blue, Ultramarine, Mangan Violet, titanium (oxide) coated mica, magnesium oxide, aluminum oxide, aluminum hydroxide, silica,- iron oxides ($\alpha$-$Fe_2O_3$, $\gamma$-$Fe_2O_3$, $Fe_3O_4$, FeO, FeOOH, etc.), yellow iron oxide, black iron oxide, iron hydroxides, titanium oxides, in particular titanium dioxide having a particle size of 0.001 to 1 μm, lower titanium oxide, cerium oxide, zirconium oxide, chromium oxide, chromium hydroxide, manganese oxide, cobalt oxide, nickel oxide, etc. and composite oxides and composite hydroxides obtained by combinations of two or more of the same, for example, silica-alumina, iron titanate, cobalt titanate, lithium cobalt titanate, cobalt aluminate, etc. In addition, the nonoxides include bismuth oxychloride, boronitride, silicon nitride, titanium nitride, and other nonoxide ceramic powders.

The silicone-treated powder of the present invention has almost all of the residual Si—H groups cross-linked or substituted with inert functional groups and has no active functional groups adsorbed on the surface, and therefore is a silicone-treated powder which is almost completely free of generation of hydrogen, exhibits sufficient hydrophobicity, and is stable and good in quality.

The amount of hydrogen generated by the Si—H groups remained on the surface of the silicone-treated powder of the present invention is not more than 0.2 ml/g of treated powder, more preferably not more than 0.1 ml/g of treated powder. If the amount of the generated hydrogen is more than 0.2 ml/g of treated powder, there is an accompanying risk at the time of production of a cosmetic or the shelf life of the product is obstructed in some cases. Further, the contact angle of water with the treated powder is not less than 100°, more preferably 100 to 130°. If the contact angle of water is less than 100°, the functions and stability of the product are sometimes hindered.

The silicone-treated powder of the present invention may be produced by the above production process a silicone-treated powder according to the present invention. The silicone compound having an Si—H group in the silicone compounds usable for the process of production includes those having the following general formula (1):

$$(R^1HSiO)_a(R^2R^3SiO)_b(R^4R^5R^6SiO_{1/2})_c \quad (1)$$

wherein $R^1$, $R^2$ and $R^3$ independently represent a hydrogen atom or a $C_1$ to $C_{10}$ hydrocarbon group, which may be substituted with at least one halogen atom, provided that $R^1$, $R^2$ and $R^3$ are not simultaneously hydrogen atoms, $R^4$, $R^5$ and $R^6$ independently represent a hydrogen atom or a $C_1$ to $C_{10}$ hydrocarbon group, which may be substituted with at least one halogen atom, a is an integer of 1 or more, b is 0 or an integer of 1 or more, c is 0 or 2, provided that $3 \leq a+b+c \leq 10000$, and the above-mentioned compound includes at least one Si—H group is preferable. Methylhydrogenpolysiloxane, a methylhydrogenpolysiloxane-dimethylpolysiloxane copolymer or tetramethylcyclotetrasiloxane is more preferable.

The silicone compounds other than silicone compounds having an Si—H group usable in the process of the present invention include, for example, dimethylpolysiloxane, octamethylcyclotetrasiloxane, etc.

The amount of the silicone compound based upon the weight of the powder usable in the process of the present invention is 0.1 to 20.0% by weight, preferably 0.5 to 15.0% by weight. If the amount is too large, the usability or applicability (e.g., smoothness etc.) naturally owned by the powder is largely lost. Contrary to this, if the amount is too small, the intended water repellency is not likely to be obtained.

In the production process of a silicone-treated powder of the present invention, in the first step (i.e., the silicone treatment step,), the silicone compound is brought into contact with the above-mentioned various powders in the form of a vapor thereof, in the form of a solution dissolved in a suitable solvent, or in the form of a liquid thereof.

When the silicone compound is brought into contact with the powder in the form of, for example, a vapor, a cyclic organosiloxane and powder are placed in separate containers in a sealed space and the tops left open or a treatment agent is mixed with a carrier gas and introduced into a chamber loaded with the powder, and therefore, no special apparatus is required.

When the silicone compound is brought into direct contact with the powder in the form of a liquid, a suitable mixer, for example, a rotary ball mixer, a vibration type ball mixer, a planetary type ball mixer, a sand mill, an attritor, a bag mill, a pony mixer, a planetary mixer, automated mortar, a Henschel mixer, etc. may be used.

When the silicone compound is brought into contact with the powder in, for example, a solution, a solution containing 0.3 to 50% by weight of the compound in a solvent such as alcohol, water, hexane, cyclohexane, and toluene is prepared, the powder is dispersed therein, then the solution heated to evaporate the solvent and the silicone compound is polymerized on the surface. This may be done using a Henschel mixer, a kneader, a mill using beads, etc.

In the production process of a silicone-treated powder of the present invention, in the second step of heat treating the powder with which the silicone compound is mixed, the heating temperature and time of the powder is 260 to 480° C. for 0.1 to 24 hours, preferably 1 to 4 hours. If the temperature less than 260° C., the Si—H groups do not easily react, while if more than 480° C., the burning and decomposition of the Si—$CH_3$ groups are promoted, and the hydrophobicity declines or disappears (hydrophilicity), that is, the silicone is converted to silica. Further, the production process of the silicone-treated powder of the present invention differs in preferable treatment conditions in the second step due to the average particle size of the material powder. That is, if the average particle size of the material powder is not more than 0.1 μm, in the second step, the silicone compound coated powder is preferably heated at 260 to 350° C., preferably 270 to 320° C. for 1 to 5 hours, preferably 2 to 3 hours. When the average particle size of the material powder is more than 0.1 μm, in the second step, the silicone compound coated powder is preferably heated at 330 to 480° C., preferably 390 to 400° C. for 1 to 5 hours, preferably 1 to 2 hours.

Further, as the heating atmosphere, it is possible to heat the powder in the air, which is an atmosphere containing moisture, or in another gas containing moisture of an extent of the moisture in the air. In addition, it is possible to adjust the powder in an atmosphere not containing moisture, then heat while adding moisture during the treatment or heating. As the device used for heating, an electric furnace, tunnel furnace, roller hearth kiln, rotary kiln, etc. may be used.

According to the present invention, there are further provided a cosmetic composition, coating composition, and resin molded article (e.g., container etc. formed by injection molding). In the production processes of these compositions, it is possible to produce products by ordinary methods other than the use of the silicone-treated powder according to the present invention, instead of powder treated by a conventional method. The cosmetic composition, coating composition, and resin molded article obtained in the present invention enable a reduction of the manufacturing costs of the products, an improvement in the quality of the products, stability of the products, and a reduction in the load in work.

EXAMPLES

The present invention will now be further illustrated by, but is by no means limited to, the following Examples. The units of formulating amounts are % by weight.

(1) In the Case of Formulating Powder Material Having an Average Particle Size of Not Less than 0.1 μm Example 1-1

500 g of sericite (average particle size: 4 μm) and 15 g of methylhydrogenpolysiloxane (product name: Silicone KF99, made by Shin-Etsu Chemical) were dissolved in 50 ml of hexane. This solution was placed in a Henschel mixer and stirred and mixed at room temperature for a predetermined time, then was placed in a dryer of 100° C. to evaporate the solvent. The powder was then placed in an electric furnace set to 400° C. in advance and heated for 3 hours to obtain a silicone-treated powder.

Example 1-2

The same procedure was followed to obtain a silicone-treated powder except for changing the sericite of Example 1-1 to titanium dioxide (average particle size: 0.5 μm).

Example 1-3

The same procedure was followed to obtain a silicone-treated powder except for changing the sericite of Example 1-1 to silica (average particle size: 5 μm).

Example 1-4

The same procedure was followed to obtain a silicone-treated powder except for changing the sericite of Example 1-1 to talc (average particle size: 15 μm).

Example 1-5

The same procedure was followed to obtain a silicone-treated powder except for changing the sericite of Example 1-1 to zinc white (average particle size: 0.5 μm).

Example 1-6

The same procedure was followed to obtain a silicone-treated powder except for changing the sericite of Example 1-1 to titanated mica (average particle size: 20 μm).

Example 1-7

The same procedure was followed to obtain a silicone-treated powder except for changing the sericite of Example 1-1 to bengara (average particle size: 0.4 μm).

Example 1-8

The same procedure was followed to obtain a silicone-treated powder except for changing the sericite of Example 1-1 to mica (average particle size: 20 μm).

Example 1-9

The same procedure was followed to obtain a silicone-treated powder except for changing the sericite of Example 1-1 to golden mica (average particle size: 30 μm).

Example 1-10

The same procedure was followed to obtain a silicone-treated powder except for changing the sericite of Example 1-1 to barium sulfate (average particle size: 10 μm).

Example 1-11

The same procedure was followed to obtain a silicone-treated powder except for changing the sericite of Example 1-1 to a titanium oxide/iron oxide composite (average particle size: 8 μm).

Example 1-12

The same procedure was followed to obtain a silicone-treated powder except for changing the sericite of Example 1-1 to bengara-coated titanated mica (average particle size: 30 μm).

Example 1-13

The same procedure was followed to obtain a silicone-treated powder except for changing the sericite of Example 1-1 to a cross-linked polysiloxane elastomer (average particle size: 5 μm).

Example 1-14

The same procedure was followed to obtain a silicone-treated powder except for changing the sericite of Example 1-1 to a silicone resin coated/cross-linked polysiloxane elastomer (average particle size: 5 μm).

Example 1-15

The same procedure was followed to obtain a silicone-treated powder except for changing the sericite of Example 1-1 to polymethylsilsesquioxane powder (average particle size: 5 μm).

Example 1-16

The same procedure was followed to obtain a silicone-treated powder except for changing the sericite of Example 1-1 to boronitride (average particle size: 20 μm).

Example 1-17

The same procedure was followed to obtain a silicone-treated powder except for changing the sericite of Example 1-1 to cerium oxide powder (average particle size: 0.6 μm).

Example 1-18

The same procedure was followed to obtain a silicone-treated powder except for changing the sericite of Example 1-1 to chromium oxide (average particle size: 0.5 μm).

Example 1-19

The same procedure was followed to obtain a silicone-treated powder except for changing the sericite of Example 1-1 to alumina (average particle size: 0.3 μm).

Example 1-20

The same procedure was followed to obtain a silicone-treated powder except for changing the sericite of Example 1-1 to bismuth oxychloride (average particle size: 3.0 μm).

Example 2-1

The method of Example 1-1 was used to coat 500 g of sericite with silicone, then this was placed in an electric furnace set to a dry nitrogen atmosphere and raised in temperature. After reaching 400° C., 10 g of water was dropped from above at a rate of 1/6 g/min. After dropping was finished, the powder was further heated for 1 hour to obtain a silicone-treated powder.

Example 2-2

The same procedure was followed to obtain a silicone-treated powder except for changing the sericite of Example 2-1 to titanium dioxide (average particle size: 0.5 μm).

Example 2-3

The same procedure was followed to obtain a silicone-treated powder except for changing the sericite of Example 2-1 to silica (average particle size: 5 μm).

Example 2-4

The same procedure was followed to obtain a silicone-treated powder except for changing the sericite of Example 2-1 to talc (average particle size: 15 μm).

Example 2-5

The same procedure was followed to obtain a silicone-treated powder except for changing the sericite of Example 2-1 to zinc white (average particle size: 0.5 μm).

Example 2-6

The same procedure was followed to obtain a silicone-treated powder except for changing the sericite of Example 2-1 to titanated mica (average particle size: 20 μm).

Example 2-7

The same procedure was followed to obtain a silicone-treated powder except for changing the sericite of Example 2-1 to bengara (average particle size: 0.4 μm).

Example 2-8

The same procedure was followed to obtain a silicone-treated powder except for changing the sericite of Example 2-1 to mica (average particle size: 20 μm).

Example 2-9

The same procedure was followed to obtain a silicone-treated powder except for changing the sericite of Example 2-1 to golden mica (average particle size: 30 μm).

Example 2-10

The same procedure was followed to obtain a silicone-treated powder except for changing the sericite of Example 2-1 to barium sulfate (average particle size: 10 μm).

Example 2-11

The same procedure was followed to obtain a silicone-treated powder except for changing the sericite of Example 2-1 to a titanium oxide/iron oxide composite (average particle size: 8 μm).

Example 2-12

The same procedure was followed to obtain a silicone-treated powder except for changing the sericite of Example 2-1 to bengara-coated mica titanium (average particle size: 30 μm).

Example 2-13

The same procedure was followed to obtain a silicone-treated powder except for changing the sericite of Example 2-1 to a cross-linked polysiloxane elastomer (average particle size: 5 μm).

Example 2-14

The same procedure was followed to obtain a silicone-treated powder except for changing the sericite of Example 2-1 to a silicone resin coated/cross-linked polysiloxane elastomer (average particle size: 5 μm).

Example 2-15

The same procedure was followed to obtain a silicone-treated powder except for changing the sericite of Example 2-1 to polymethylsilsesquioxane powder (average particle size: 5 μm).

Example 2-16

The same procedure was followed to obtain a silicone-treated powder except for changing the sericite of Example 2-1 to boronitride (average particle size: 20 μm).

Example 2-17

The same procedure was followed to obtain a silicone-treated powder except for changing the sericite of Example 2-1 to cerium oxide powder (average particle size: 0.6 μm).

Example 2-18

The same procedure was followed to obtain a silicone-treated powder except for changing the sericite of Example 2-1 to chromium oxide (average particle size: 0.5 μm).

Example 2-19

The same procedure was followed to obtain a silicone-treated powder except for changing the sericite of Example 2-1 to alumina (average particle size: 0.3 μm).

Example 2-20

The same procedure was followed to obtain a silicone-treated powder except for changing the sericite of Example 2-1 to bismuth oxychloride (average particle size: 3.0 μm).

(2) In the Case of the Formulating Powder Material Having an Average Particle Size of Not More than 0.1 μm

Example 3-1

500 g of alumina-coated finely divided particle titanium dioxide (average particle size: 0.015 μm) and 25 g of methylhydrogenpolysiloxane were dissolved in 50 ml of hexane. This solution was placed in a Henschel mixer and stirred and mixed at room temperature for a predetermined time, then was placed in a dryer of 100° C. to evaporate the solvent. Next, the powder was placed in an oven set to 270° C. in advance and heated for 3 hours to obtain a silicone-treated powder.

Example 3-2

The same procedure was followed to obtain a silicone-treated powder except for changing the powder of Example 3-1 to finely divided particle zinc oxide (average particle size: 0.01 μm).

Example 3-3

The same procedure was followed to obtain a silicone-treated powder except for changing the powder of Example 3-1 to finely divided particle cerium oxide (average particle size: 0.01 μm).

Example 4-1

500 g of finely divided particle titanium dioxide (average particle size: 0.01 μm) and 35 g of tetramethylcyclotetrasiloxane were placed in a desiccator and allowed to stand at 50° C. for one day, the powder was then heated by passing through a tunnel furnace set to 300° C. in advance (nitrogen atmosphere containing moisture) over 10 minutes to obtain a silicone-treated powder.

Example 4-2

The same procedure was followed to obtain a silicone-treated powder except for changing the finely divided particle titanium dioxide of Example 4-1 to finely divided particle zinc oxide (average particle size: 0.01 μm).

Example 4-3

The same procedure was followed to obtain a silicone-treated powder except for changing the finely divided particle titanium dioxide of Example 4-1 to bengara (average particle size: 0.08 μm).

Example 4-4

The same procedure was followed to obtain a silicone-treated powder except for changing the finely divided particle titanium dioxide of Example 4-1 to carbon black (average particle size: 0.05 μm).

Example 4-5

The same procedure was followed to obtain a silicone-treated powder except for changing the finely divided particle titanium dioxide of Example 4-1 to titanium mica (average particle size: 0.08 μm).

Example 4-6

The same procedure was followed to obtain a silicone-treated powder except for changing the finely divided particle titanium dioxide of Example 4-1 to a titanium dioxide/iron oxide sintered composite (average particle size: 0.07 μm).

Example 4-7

The same procedure was followed to obtain a silicone-treated powder except for changing the finely divided particle titanium dioxide of Example 4-1 to chromium oxide (average particle size: 0.09 μm).

Example 4-8

The same procedure was followed to obtain a silicone-treated powder except for changing the finely divided particle titanium dioxide of Example 4-1 to Ultramarine (average particle size: 0.07 μm).

Example 4-9

The same procedure was followed to obtain a silicone-treated powder except for changing the finely divided particle titanium dioxide of Example 4-1 to finely divided particle cerium dioxide (average particle size: 0.01 μm).

Example 5-1

100 g of finely divided particle titanium dioxide (average particle size: 0.015 μm), 300 g of toluene, 7 g of a methylhydrogenpolysiloxane-dimethylsiloxane copolymer (product name: Silicone KF9901), and 200 g of zirconia beads having a diameter of 1 mm φ were placed in a 1 liter cup made of Teflon and stirred and mixed for a predetermined time at a predetermined temperature, then the toluene was distilled off in vacuo and the remainder was heated under the temperature conditions of Example 3 (270° C., 3 hours) to obtain a silicone-treated powder.

Example 5-2

The same procedure was followed to obtain a silicone-treated powder except for changing the powder of Example 5-1 to finely divided particle zinc oxide (average particle size: 0.01 μm).

Example 5-3

The same procedure was followed to obtain a silicone-treated powder except for changing the powder of Example 5-1 to finely divided particle cerium oxide (average particle size: 0.01 μm).

Comparative Examples 1-1 to 1-20

The same procedures were followed by the same powders and the same methods as the corresponding Examples 1 to obtain silicone-treated powders except for not performing the heating step.

Comparative Examples 2-1 to 2-20

The same procedures were followed by the same powders and the same methods as the corresponding Examples 1 to obtain silicone-treated powders except for heating at 300° C. for 3 hours.

Comparative Examples 3-1 to 3-20

The same procedures were followed by the same powders and the same methods as the corresponding Examples 1 to obtain silicone-treated powders except for heating at 550° C. for 3 hours.

Comparative Examples 4-1 to 4-20

The same procedures were followed by the same powders and the same methods as the corresponding Examples 2 to obtain silicone-treated powders except for heating at 300° C. for 3 hours.

Comparative Examples 5-1 to 5-20

The same procedures were followed by the same powders and the same methods as the corresponding Examples 2 to obtain silicone-treated powders except for heating at 550° C. for 3 hours.

Comparative Examples 6-1 to 6-3

The same procedures were followed by the same powders and the same methods as the corresponding Examples 3 to obtain silicone-treated powders except for heating at 200° C. for 3 hours.

Comparative Examples 7-1 to 7-3

The same procedures were followed by the same powders and the same methods as the corresponding Examples 3 to obtain silicone-treated powders except for heating at 550° C. for 3 hours.

Comparative Examples 8-1 to 8-9

The same procedures were followed by the same powders and the same methods as the corresponding Examples 4 to obtain silicone-treated powders except for heating at 200° C. for 3 hours.

Comparative Examples 9-1 to 9-9

The same procedures were followed by the same powders and the same methods as the corresponding Examples 4 to obtain silicone-treated powders except for heating at 550° C. for 3 hours.

Comparative Examples 10-1 to 10-3

The same procedures were followed by the same powders and the same methods as the corresponding Examples 5 to obtain silicone-treated powders except for heating at 200° C. for 3 hours.

Comparative Examples 11-1 to 11-3

The same procedures were followed by the same powders and the same methods as the corresponding Examples 5 to obtain silicone-treated powders except for heating at 550° C. for 3 hours.

The amounts of generation of hydrogen gas of the silicone-treated powders obtained in the Examples and the Comparative Examples and their contact angles with water were determined by the following methods:

The generation amount of hydrogen gas was determined by the gas burette method. 2 g of silicone-treated powder and about 40 ml of alcohol were placed in a three-necked flask. About 1 ml of 10% NaOH aqueous solution was dropped in this by a closed system to cause the production of hydrogen gas and the amount of production of hydrogen (ml) per g was calculated.

The contact angle with water was determined by using an IR tableting machine (diameter 13 mm) to prepare pellets of the silicone-treated powders of the Examples and Comparative Examples and then using an automatic contact angle meter (Model CA-Z) made by Kyowa Kaimen Kagaku (average value for three measurements).

The results of the determination of the amounts of hydrogen generation and the contact angles with water in the silicone-treated powders obtained in the Examples and the Comparative Examples are shown in Tables 1 to 7. The smaller the amount of residual Si—H groups acting as the source of the generation of hydrogen gas and the higher the contact angle, the better.

TABLE 1

| Example | Amount of generation of residual hydrogen (ml/g) | Contact angle (degree) |
|---|---|---|
| Ex. 1-1 | 0.08 | 115 |
| Ex. 1-2 | 0.01 | 120 |
| Ex. 1-3 | 0.10 | 107 |
| Ex. 1-4 | 0.03 | 109 |
| Ex. 1-5 | 0.02 | 115 |
| Ex. 1-6 | 0.01 | 116 |
| Ex. 1-7 | 0.04 | 122 |
| Ex. 1-8 | 0.05 | 117 |
| Ex. 1-9 | 0.03 | 107 |
| Ex. 1-10 | 0.12 | 115 |
| Ex. 1-11 | 0.03 | 120 |
| Ex. 1-12 | 0.08 | 111 |
| Ex. 1-13 | 0.17 | 123 |
| Ex. 1-14 | 0.11 | 119 |
| Ex. 1-15 | 0.07 | 126 |
| Ex. 1-16 | 0.06 | 124 |
| Ex. 1-17 | 0.02 | 121 |
| Ex. 1-18 | 0.03 | 118 |
| Ex. 1-19 | 0.05 | 120 |
| Ex. 1-20 | 0.11 | 128 |
| Ex. 2-1 | 0.03 | 120 |
| Ex. 2-2 | 0.0 | 110 |
| Ex. 2-3 | 0.03 | 115 |
| Ex. 2-4 | 0.01 | 112 |
| Ex. 2-5 | 0.01 | 120 |
| Ex. 2-6 | 0.0 | 123 |
| Ex. 2-7 | 0.02 | 107 |
| Ex. 2-8 | 0.03 | 124 |
| Ex. 2-9 | 0.01 | 120 |
| Ex. 2-10 | 0.0 | 105 |
| Ex. 2-11 | 0.0 | 121 |
| Ex. 2-12 | 0.10 | 120 |
| Ex. 2-13 | 0.08 | 104 |
| Ex. 2-14 | 0.05 | 125 |
| Ex. 2-15 | 0.03 | 117 |
| Ex. 2-16 | 0.02 | 129 |

TABLE 1-continued

| Example | Amount of generation of residual hydrogen (ml/g) | Contact angle (degree) |
| --- | --- | --- |
| Ex. 2-17 | 0.0 | 128 |
| Ex. 2-18 | 0.0 | 117 |
| Ex. 2-19 | 0.01 | 126 |
| Ex. 2-20 | 0.04 | 129 |

TABLE 2

| Comp. Example | Amount of generation of residual hydrogen (ml/g) | Contact angle (degree) |
| --- | --- | --- |
| Comp. Ex. 1-1 | 2.81 | 120 |
| Comp. Ex. 1-2 | 1.35 | 122 |
| Comp. Ex. 1-3 | 2.45 | 109 |
| Comp. Ex. 1-4 | 2.08 | 110 |
| Comp. Ex. 1-5 | 1.55 | 115 |
| Comp. Ex. 1-6 | 1.87 | 117 |
| Comp. Ex. 1-7 | 2.14 | 120 |
| Comp. Ex. 1-8 | 2.00 | 114 |
| Comp. Ex. 1-9 | 2.33 | 105 |
| Comp. Ex. 1-10 | 2.52 | 115 |
| Comp. Ex. 1-11 | 1.10 | 120 |
| Comp. Ex. 1-12 | 1.34 | 111 |
| Comp. Ex. 1-13 | 3.02 | 123 |
| Comp. Ex. 1-14 | 2.43 | 119 |
| Comp. Ex. 1-15 | 2.59 | 126 |
| Comp. Ex. 1-16 | 2.20 | 124 |
| Comp. Ex. 1-17 | 1.55 | 121 |
| Comp. Ex. 1-18 | 1.81 | 118 |
| Comp. Ex. 1-19 | 1.12 | 120 |
| Comp. Ex. 1-20 | 1.76 | 128 |
| Comp. Ex. 2-1 | 1.88 | 117 |
| Comp. Ex. 2-2 | 0.98 | 125 |
| Comp. Ex. 2-3 | 1.65 | 103 |
| Comp. Ex. 2-4 | 1.22 | 114 |
| Comp. Ex. 2-5 | 1.04 | 107 |
| Comp. Ex. 2-6 | 1.13 | 124 |
| Comp. Ex. 2-7 | 1.64 | 127 |
| Comp. Ex. 2-8 | 1.33 | 110 |
| Comp. Ex. 2-9 | 1.79 | 104 |

TABLE 2-continued

| Comp. Example | Amount of generation of residual hydrogen (ml/g) | Contact angle (degree) |
| --- | --- | --- |
| Comp. Ex. 2-10 | 1.50 | 113 |
| Comp. Ex. 2-11 | 0.68 | 121 |
| Comp. Ex. 2-12 | 0.90 | 120 |
| Comp. Ex. 2-13 | 1.98 | 104 |
| Comp. Ex. 2-14 | 1.07 | 125 |
| Comp. Ex. 2-15 | 1.36 | 117 |
| Comp. Ex. 2-16 | 1.25 | 129 |
| Comp. Ex. 2-17 | 0.73 | 128 |
| Comp. Ex. 2-18 | 0.88 | 117 |
| Comp. Ex. 2-19 | 0.55 | 126 |
| Comp. Ex. 2-20 | 0.90 | 129 |

TABLE 3

| Comp. Example | Amount of generation of residual hydrogen (ml/g) | Contact angle (degree) |
| --- | --- | --- |
| Comp. Ex. 3-1 | 0.0 | 0 |
| Comp. Ex. 3-2 | 0.0 | 0 |
| Comp. Ex. 3-3 | 0.0 | 0 |
| Comp. Ex. 3-4 | 0.0 | 0 |
| Comp. Ex. 3-5 | 0.0 | 0 |
| Comp. Ex. 3-6 | 0.0 | 0 |
| Comp. Ex. 3-7 | 0.0 | 0 |
| Comp. Ex. 3-8 | 0.0 | 0 |
| Comp. Ex. 3-9 | 0.0 | 0 |
| Comp. Ex. 3-10 | 0.0 | 0 |
| Comp. Ex. 3-11 | 0.0 | 0 |
| Comp. Ex. 3-12 | 0.0 | 0 |
| Comp. Ex. 3-13 | 0.0 | 0 |
| Comp. Ex. 3-14 | 0.0 | 0 |
| Comp. Ex. 3-15 | 0.0 | 0 |
| Comp. Ex. 3-16 | 0.0 | 0 |
| Comp. Ex. 3-17 | 0.0 | 0 |
| Comp. Ex. 3-18 | 0.0 | 0 |
| Comp. Ex. 3-19 | 0.0 | 0 |
| Comp. Ex. 3-20 | 0.0 | 0 |

TABLE 3-continued

| Comp. Example | Amount of generation of residual hydrogen (ml/g) | Contact angle (degree) |
|---|---|---|
| Comp. Ex. 4-1 | 0.68 | 129 |
| Comp. Ex. 4-2 | 0.55 | 116 |
| Comp. Ex. 4-3 | 0.46 | 110 |
| Comp. Ex. 4-4 | 0.70 | 103 |
| Comp. Ex. 4-5 | 0.51 | 128 |
| Comp. Ex. 4-6 | 0.39 | 110 |
| Comp. Ex. 4-7 | 0.80 | 130 |
| Comp. Ex. 4-8 | 0.95 | 103 |
| Comp. Ex. 4-9 | 1.18 | 111 |
| Comp. Ex. 4-10 | 0.77 | 120 |
| Comp. Ex. 4-11 | 0.43 | 113 |
| Comp. Ex. 4-12 | 0.69 | 108 |
| Comp. Ex. 4-13 | 1.02 | 110 |
| Comp. Ex. 4-14 | 0.54 | 131 |
| Comp. Ex. 4-15 | 0.79 | 114 |
| Comp. Ex. 4-16 | 1.20 | 121 |
| Comp. Ex. 4-17 | 0.41 | 117 |
| Comp. Ex. 4-18 | 0.67 | 124 |
| Comp. Ex. 4-19 | 0.37 | 126 |
| Comp. Ex. 4-20 | 0.84 | 116 |

TABLE 4

| Comp. Example | Amount of generation of residual hydrogen (ml/g) | Contact angle (degree) |
|---|---|---|
| Comp. Ex. 5-1 | 0.0 | 0 |
| Comp. Ex. 5-2 | 0.0 | 0 |
| Comp. Ex. 5-3 | 0.0 | 0 |
| Comp. Ex. 5-4 | 0.0 | 0 |
| Comp. Ex. 5-5 | 0.0 | 0 |
| Comp. Ex. 5-6 | 0.0 | 0 |
| Comp. Ex. 5-7 | 0.0 | 0 |
| Comp. Ex. 5-8 | 0.0 | 0 |
| Comp. Ex. 5-9 | 0.0 | 0 |
| Comp. Ex. 5-10 | 0.0 | 0 |
| Comp. Ex. 5-11 | 0.0 | 0 |
| Comp. Ex. 5-12 | 0.0 | 0 |
| Comp. Ex. 5-13 | 0.0 | 0 |
| Comp. Ex. 5-14 | 0.0 | 0 |
| Comp. Ex. 5-15 | 0.0 | 0 |
| Comp. Ex. 5-16 | 0.0 | 0 |
| Comp. Ex. 5-17 | 0.0 | 0 |
| Comp. Ex. 5-18 | 0.0 | 0 |
| Comp. Ex. 5-19 | 0.0 | 0 |
| Comp. Ex. 5-20 | 0.0 | 0 |

TABLE 5

| | Amount of generation of residual hydrogen (ml/g) | Contact angle (degree) |
|---|---|---|
| Example | | |
| Ex. 3-1 | 0.17 | 113 |
| Ex. 3-2 | 0.04 | 122 |
| Ex. 3-3 | 0.11 | 119 |
| Comp. Example | | |
| Comp. Ex. 6-1 | 0.38 | 119 |
| Comp. Ex. 6-2 | 0.26 | 128 |
| Comp. Ex. 6-3 | 0.36 | 115 |
| Comp. Ex. 7-1 | 0.0 | 0 |
| Comp. Ex. 7-2 | 0.0 | 0 |
| Comp. Ex. 7-3 | 0.0 | 0 |

TABLE 6

| | Amount of generation of residual hydrogen (ml/g) | Contact angle (degree) |
|---|---|---|
| Example | | |
| Ex. 4-1 | 0.19 | 123 |
| Ex. 4-2 | 0.17 | 117 |
| Ex. 4-3 | 0.11 | 115 |
| Ex. 4-4 | 0.08 | 110 |
| Ex. 4-5 | 0.16 | 118 |
| Ex. 4-6 | 0.15 | 116 |

TABLE 6-continued

| | Amount of generation of residual hydrogen (ml/g) | Contact angle (degree) |
|---|---|---|
| Ex. 4-7 | 0.19 | 118 |
| Ex. 4-8 | 0.14 | 123 |
| Ex. 4-9 | 0.07 | 121 |
| Comp. Example | | |
| Comp. Ex. 8-1 | 0.50 | 126 |
| Comp. Ex. 8-2 | 0.89 | 120 |
| Comp. Ex. 8-3 | 0.73 | 113 |
| Comp. Ex. 8-4 | 0.44 | 116 |
| Comp. Ex. 8-5 | 0.53 | 126 |
| Comp. Ex. 8-6 | 0.67 | 110 |
| Comp. Ex. 8-7 | 0.90 | 127 |
| Comp. Ex. 8-8 | 0.70 | 121 |
| Comp. Ex. 8-9 | 0.56 | 117 |
| Comp. Ex. 9-1 | 0.0 | 0 |
| Comp. Ex. 9-2 | 0.0 | 0 |
| Comp. Ex. 9-3 | 0.0 | 0 |
| Comp. Ex. 9-4 | 0.0 | 0 |
| Comp. Ex. 9-5 | 0.0 | 0 |
| Comp. Ex. 9-6 | 0.0 | 0 |
| Comp. Ex. 9-7 | 0.0 | 0 |
| Comp. Ex. 9-8 | 0.0 | 0 |
| Comp. Ex. 9-9 | 0.0 | 0 |

TABLE 7

| | Amount of generation of residual hydrogen (ml/g) | Contact angle (degree) |
|---|---|---|
| Example | | |
| Ex. 5-1 | 0.10 | 115 |
| Ex. 5-2 | 0.0 | 120 |
| Ex. 5-3 | 0.02 | 115 |
| Comparative Example | | |
| Comp. Ex. 10-1 | 0.55 | 120 |
| Comp. Ex. 10-2 | 0.25 | 121 |
| Comp. Ex. 10-3 | 0.37 | 119 |
| Comp. Ex. 11-1 | 0 | 0 |
| Comp. Ex. 11-2 | 0 | 0 |
| Comp. Ex. 11-3 | 0 | 0 |

Example 6

Foundation

| | Ingredient | wt % |
|---|---|---|
| (1) | Treated powder of Example 1-1 | 35.0 |
| (2) | Treated powder of Example 1-2 | 13.0 |
| (3) | Treated powder of Example 1-4 | 24.7 |
| (4) | Treated powder of Example 1-10 | 10.0 |
| (5) | Treated powder of Example 1-7 | 1.0 |
| (6) | Treated powder of Example 1-8 | 2.5 |
| (7) | Treated powder of Example 1-9 | 0.1 |
| (8) | Liquid paraffin | 8.0 |
| (9) | Sorbitan sesquioleate | 3.5 |
| (10) | Glycerol | 2.0 |
| (11) | Ethyl paraben | 0.2 |

(Process of Production)

The ingredients (1) to (7) were mixed and pulverized by a pulverizer. The resultant mixture was transferred to a high speed blender, then the ingredient (10) was added and the result mixed. Separately from this, the ingredients (8), (9), and (11) were homogeneously mixed, then this was added to the above mixture and further homogeneously mixed. The mixture was then treated by a pulverizer and passed through a sieve to obtain a standard particle size, then the resultant powder was compression molded to obtain a solid foundation. The foundation thus obtained had a good hold.

Comparative Example 12

The same procedure was followed as in Example 6 to prepare a foundation except for replacing ingredients (1) to (7) in the foundation prepared in Example 6 with the ingredients of the corresponding Comparative Example 1.

Comparative Example 13

The same procedure was followed as in Example 6 to prepare a foundation except for replacing the ingredients (1) to (7) in the foundation prepared in Example 6 with the ingredients of the corresponding Comparative Example 2.

Comparative Example 14

The same procedure was followed as in Example 6 to prepare a foundation except for replacing the ingredients (1) to (7) in the foundation prepared in Example 6 with the ingredients of the corresponding Comparative Example 3.

(1) Evaluation of Use

Samples held at 50° C. for one month were evaluated by the following criteria as for various aspects of usability (removability, covering power, slip, use by a sponge wet with water, cracking of the pack surface, hold, transparency, and water resistance) by a panel of 20 women:

(Evaluation Criteria)

Very good: At least 17 women responded sample was good
Good: 12 to 16 women responded sample was good
Fair: 9 to 11 women responded sample was good
Poor: 5 to 8 women responded sample was good
Very poor: 4 or less women responded sample was good (2) Evaluation of Shelf Life Samples held at 50° C. for one month were compared for stability.

(3) Evaluation of SPF (UV Blocking Effect)

Samples held at 50° C. for one month were measured for in vitro SPF value by the Spectro Radiometer method.

The results of evaluation of the usability of the samples of Example 6 and Comparative Examples 12 to 14 by the above criteria after being held at 50° C. for one month are shown in Table 8.

TABLE 8

|  | Ex. 6 | Comp. Ex. 12 | Comp. Ex. 13 | Camp. Ex. 14 |
|---|---|---|---|---|
| Removability | Very good | Fair | Fair | Fair |
| Covering power | Very good | Fair | Fair | Fair |
| Slip | Good | Good | Good | Poor |
| Use on sponge wet with water | No problem | No problem | No problem | Caking |
| Cracking of pack surface | None | Yes | Yes | None |

As will be understood from Table 8, Example 6 could be applied with no problem even using water as a dual use type and was superior in shelf life.

Example 7

Emulsion Foundation

|  | Ingredient | wt % |
|---|---|---|
| (A) | Ion exchanged water | 43.5 |
|  | Sodium chondroitin sulfate | 1.0 |
|  | 1,3-butylene glycol | 3.0 |
|  | Methyl paraben | q.s. |
| (B) | Dimethylpolysiloxane (20 cs) | 16.0 |
|  | Decamethylcyclopentasiloxane | 5.0 |
|  | Silicone resin | 1.0 |
|  | Cetylisooctanate | 1.0 |
|  | Polyoxyalkylene modified organopolysiloxane (modification rate 20%) | 4.0 |
|  | Antioxidant | q.s. |
|  | Fragrance | q.s |
| (C) | Treated powder of Example 1-8 | 1.0 |
|  | Treated powder of Example 2-3 | 0.45 |
|  | Treated powder of Example 2-4 | 0.2 |
|  | Treated powder of Example 1-2 | 11.7 |
|  | Treated powder of Example 1-1 | 9.65 |
|  | Treated powder of Example 2-7 | 2.0 |

(Process of Production)

The ingredients (B) were heated to melt, then the powders of ingredient (C) were added and dispersed in them. Further, the ingredients (A) melted and heated in advance were added to make an emulsion, then the emulsion was cooled to room temperature to obtain an emulsion foundation. The obtained emulsion foundation had a good hold.

Comparative Example 15

The same procedure was followed as in Example 7 to obtain an emulsion foundation except for replacing the ingredients (C) in the emulsion foundation prepared in Example 7 with the ingredients of the corresponding Comparative Example 1.

Comparative Example 16

The same procedure was followed as in Example 7 to obtain an emulsion foundation except for replacing the ingredients (C) in the emulsion foundation prepared in Example 7 with the ingredients of the corresponding Comparative Example 2.

Comparative Example 17

The same procedure was followed as in Example 7 to obtain an emulsion foundation except for replacing the ingredients (C) in the emulsion foundation prepared in Example 7 with the ingredients of the corresponding Comparative Example 3.

The results of evaluation of the usability of the samples and shelf life of Example 7 and Comparative Examples 15 to 17 by the above criteria after being held at 50° C. for one month are shown in Table 9.

TABLE 9

|  | Ex. 7 | Comp. Ex. 15 | Comp. Ex. 16 | Comp. Ex. 17 |
|---|---|---|---|---|
| Covering power | Good | Fair | Fair | Fair |
| Slip | Good | Fair | Fair | Poor |
| Hold | Very good | Good | Good | Very poor |
| Shelf life | No problem | Container swelled | Container swelled | No problem |

As will be understood from Table 9, the emulsion foundation prepared in Example 7 had a good hold and was superior in shelf life as well.

Example 8

Emulsion Foundation (Solid Type)

|  | Ingredient | wt % |
|---|---|---|
| (A) | Ion exchanged water | 43.5 |
|  | Sodium glutamate | 1.0 |
|  | 1,3-butylene glycol | 5.0 |
|  | Methyl paraben | q.s. |
| (B) | Dimethylpolysiloxane (20 cs) | 4.0 |
|  | Decamethylcyclopentasiloxane | 16.0 |
|  | Silicone resin | 1.0 |
|  | Cetyl isooctanate | 1.0 |
|  | Polyoxyalkylene modified organopolysiloxane (modification rate 20%) | 4.0 |
|  | Antioxidant | q.s. |
|  | Fragrance | q.s |
| (C) | Wax | 5.0 |
| (D) | Treated powder of Example 1-2 | 8.0 |
|  | Treated powder of Example 2-7 | 0.5 |
|  | Treated powder of Example 3-1 | 6.0 |
|  | Treated powder of Example 2-10 | 3.0 |
|  | Silicone-treated black iron oxide | 0.1 |
|  | Silicone-treated yellow iron oxide | 1.4 |

(Process of Production)

The ingredients (B) were heated, then the ingredient (C) was added and the mixture made to completely melt. Next, the powders of ingredients (D) were added and dispersed while heating. Further, the ingredients (A) melted and heated in advance were added to create an emulsion. This was then cooled to room temperature to obtain an emulsion foundation (solid type). The obtained emulsion foundation had a good hold.

Comparative Example 18

The same procedure was followed as in Example 8 to obtain an emulsion foundation except for replacing the ingredients (D) in the emulsion foundation (solid type) prepared in Example 8 with the ingredients of the corresponding Comparative Example 1 (for Example 3-1, Comparative Example 6-1).

Comparative Example 19

The same procedure was followed as in Example 8 to obtain an emulsion foundation (solid type) except for replacing the ingredients (D) in the emulsion foundation prepared in Example 8 with the ingredients of the corresponding Comparative Example 2 (for Example 3-1, Comparative Example 7-1)

The results of evaluation of the usability of the samples and shelf life of Example 8 and Comparative Examples 18 to 19 by the above criteria after being held at 50° C. for one month are shown in Table 10.

TABLE 10

|  | Ex. 8 | Comp. Ex. 18 | Comp. Ex. 19 |
| --- | --- | --- | --- |
| Covering power | Good | Fair | Fair |
| Slip | Good | Fair | Poor |
| Hold | Very good | Good | Very poor |
| Shelf life | No problem | Container swelled | No problem |

As will be understood from Table 10, the emulsion foundation prepared in Example 8 had a good hold and was superior in shelf life as well.

Example 9

Pressed Powder

|  | Ingredient | wt % |
| --- | --- | --- |
| (1) | Treated powder of Example 1-5 | 30.0 |
| (2) | Treated powder of Example 1-4 | 65.8 |
| (3) | Iron oxide pigment | 0.1 |
| (4) | Squalane | 2.0 |
| (5) | 2-ethylhexyl palmitate | 2.0 |
| (6) | Fragrance | 0.1 |

(Process of Production)

The ingredients (1), (2), and (3) were mixed in a Henschel mixer, then a heated mixture of the ingredients (4) and (5) was sprayed on the mixture. These were mixed, then pulverized, then molded into a dish to obtain a pressed powder. The obtained pressed powder had a moisture retention effect, a good hold, and superior shelf life as well.

Example 10

Body Powder

|  | Ingredient | wt % |
| --- | --- | --- |
| (A) | Treated powder of Example 1-4 | 89.0 |
|  | Treated powder of Example 1-6 | 10.0 |
|  | Coloring pigment | q.s. |
| (B) | Treated powder of Example 1-5 | 3.0. |
| (C) | Magnesium stearate | 4.0 |
|  | Liquid paraffin | 1.0 |
|  | Bactericide | q.s. |
| (D) | Fragrance | q.s. |

(Process of Production)

The ingredients (A) were mixed by a blender, then the ingredient (B) was added and mixed well. The ingredients (C) were then added, the coloring adjusted, then the ingredient (D) was sprayed on and then homogeneously mixed in. The mixture was pulverized by a pulverizer, then passed through a sieve to obtain the body powder. The body powder thus obtained had a high water repellency.

Example 11

Lipstick

|  | Ingredient | wt % |
| --- | --- | --- |
| (1) | Hydrocarbon wax | 3.0 |
| (2) | Carnauba wax | 1.0 |
| (3) | Glyceryl isostearate | 40.0 |
| (4) | Liquid paraffin | 45.8 |
| (5) | Treated powder of Example 1-3 | 4.0 |
| (6) | Mixed treated powders of Example 1-1 and Example 1-7 | 6.0 |
| (7) | Fragrance | 0.2 |

(Process of Production)

The ingredients (1) to (4) were melted at 85° C., then the ingredients (5) and (6) were added while stirring. Next, while stirring, the ingredient (7) was added and the mixture packed into a container. The obtained lipstick was superior in moisture retention effect.

Example 12

Water-in-Oil Type Emulsion Sunscreen

|  | Ingredient | wt % |
| --- | --- | --- |
| (A) | Decamethylcyclopentasiloxane | Bal. |
|  | Dimethylpolysiloxane | 5.0 |
|  | Polyoxyethylene.methylpolysiloxane copolymer | 3.0 |
|  | Organic modified bentonite | 1.0 |
| (B) | Treated powder of Example 1-4 | 10.0 |
|  | Treated powder of Example 2-1 | 7.0 |
|  | Treated powder of Example 2-2 | 10.0 |
|  | Silicone elastic powder | 3.0 |
|  | Fragrance | q.s. |
|  | Antioxidant | q.s. |
| (C) | Ion exchanged water | 35.0 |
|  | Glycerin | 5.0 |
|  | Preservative | q.s. |

(Process of Production)

The (A) phase was heated to melt, then the (B) phase was added and the mixture was homogeneously dispersed by a homomixer. Then phase (C) was added gradually and stirred well, then homogeneously emulsified by a homomixer. This was then stirred and cooled to obtain a water-in-oil type emulsion sunscreen. The obtained sunscreen had a high sunburn preventing effect.

Comparative Example 20

The same procedure was performed as in Example 12 to prepare a water-in-oil type emulsion sunscreen except for replacing the treated powder portion in the ingredients (B) in the water-in-oil type emulsion sunscreen prepared in Example 12 with the ingredients of the corresponding Comparative Example 1.

Comparative Example 21

The same procedure was performed as in Example 12 to prepare a water-in-oil type emulsion sunscreen except for replacing the treated powder portion in the ingredients (B) in the water-in-oil type emulsion sunscreen prepared in Example 12 with the ingredients of the corresponding Comparative Example 2.

Comparative Example 22

The same procedure was performed as in Example 12 to prepare a water-in-oil type emulsion sunscreen except for replacing the treated powder portion in the ingredients (B) in the water-in-oil type emulsion sunscreen prepared in Example 12 with the ingredients of the corresponding Comparative Example 3.

The results of evaluation of the usability, the SPF value, and the shelf life of the samples of Example 12 and Comparative Examples 20 to 22 by the above criteria after being held at 50° C. for one month are shown in Table Table 11.

TABLE 11

|  | Ex. 12 | Comp. Ex. 20 | Comp. Ex. 21 | Comp. Ex. 22 |
|---|---|---|---|---|
| Slip | Good | Fair | Fair | Poor |
| Transparency | Very good | Good | Good | Fair |
| Water resistance | Very good | Good | Good | Very poor |
| SPF | 44 | 41 | 42 | 22 |
| Shelf life | No problem | Container swelled | Container swelled | No problem |

Comparative Example 20 and Comparative Example 21 were good in usability to a certain extent, but the containers swelled along with time, Comparative Example 22 suffered from aggregation of the powder due to the hydrophilicity and had a low SPF, but Example 12 was superior in all of the usability, shelf life, and SPF value.

Example 13

Coating Composition 20 g of the treated powder obtained in Example 1-2 and 18 g of acrylic resin solution (Mn=48,200, Mn/Mw=2.56) were mixed together with 70 g of glass beads by a paint shaker for 20 minutes to obtain a coating composition. The coating composition obtained was superior in stability over time.

Example 14

Container

The treated powder obtained in Example 2-1 was mixed in an amount of 2% by weight in polyethylene. This was then injected molded into a white polystyrene wide mouth vase.

Comparative Example 23

As a Comparative Example, the same procedure was used as in Example 14 for injection molding except for using finely divided particle titanium dioxide not treated with silicone.

4 cm×4 cm sized pieces were cut from the wide mouth vases of Example 14 and Comparative Example 23 and measured for UV absorption spectra (diffusion reflection method), whereupon the piece obtained from Example 14 was observed to have a higher UV absorption effect.

As explained in detail above, the silicone-treated powder of the present invention was stable in quality and free from any unpleasant odor from the powder. Further, the silicone-treated powder of the present invention can be used for cosmetic compositions, paints, resin shaped articles, and a broad range of other products.

Further, according to the production process of a silicone-treated powder of the present invention, there are the advantages that it is possible to produce a good quality silicone-treated powder by a simple process and possible to provide it at a low production cost.

The invention claimed is:

1. A process for producing a silicone-treated hydrophobic powder comprising the steps of:
   coating a surface of a starting powder with (1) a silicone compound having at least one Si—H group or (2) a mixture of the silicone compound (I) and a silicone compound not having an Si—H group, as a first step; and then
   heating the silicone compound coated powder at a temperature of 260 to 480° C. for 0.1 to 24 hours, as a second step, whereby the Si—H groups of silicone compound (I) are cross-linked,
   wherein said silicone compound having an Si—H group is a silicone compound having the formula (I):

$$(R^1HSiO)_a(R^2R^3SiO)_b(R^4R^5R^6SiO)_{1/2})_c \qquad (I)$$

wherein $R^1$, $R^2$, and $R^3$ independently represent a hydrogen atom or a $C_1$ to $C_{10}$ hydrocarbon group, which may be substituted with at least one halogen atom, provided that $R^1$, $R^2$ and $R^3$ are not simultaneously hydrogen atoms, $R^4$, $R^5$ and $R^6$ independently represent a hydrogen atom or a $C_1$ to $C_{10}$ hydrocarbon group, which may be substituted with at least one halogen atom, a is an integer of 1 or more, b is an integer of 1 or more, c is 2, provided that $3 \leq a + b + c \leq 10,000$, and the compound has at least one Si—H group.

2. A process for producing a silicone-treated hydrophobic powder as claimed in claim 1, wherein, when an average particle size of the starting powder is not more than 0.1 µm, the silicone compound coated powder is heated in the second step at a temperature of 260 to 320° C. for 1 to 5 hours.

3. A process for producing a silicone-treated hydrophobic powder as claimed in claim 1, wherein, when an average particle size of the starting powder is more than 0.1 µm, the silicone compound coated powder is heated in the second step at a temperature of 330 to 480° C. for 1 to 5 hours.

4. A process for producing a silicone-treated hydrophobic powder as claimed in claim 1, wherein said silicone compound having an Si—H group is a methylhydrogenpolysiloxane-dimethylpolysiloxane copolymer.

5. A process for producing a silicone-treated hydrophobic powder as claimed in claim 1, wherein said heat treatment in the second step is carried out in the air or under an atmosphere of one or more other gases containing moisture of at least an extent of the moisture in the air or under an atmosphere not containing moisture while adding moisture.

6. A silicone-treated hydrophobic powder produced by a process comprising the steps of:
   coating a surface of a starting powder with (1) a silicone compound having at least one Si—H group or (2) a mixture of the silicone compound (I) and a silicone compound not having an Si—H group, as a first step; and then
   heating the silicone compound coated powder at a temperature of 260 to 480° C. for 0.1 to 24 hours, as a second step, whereby the Si—H groups of silicone compound (I) are cross-linked,
   wherein said silicone compound having an Si—H group is a silicone compound having the formula (I):

$$(R^1HSiO)_a(R^2R^3SiO)_b(R^4R^5R^6SiO)_{1/2})_c \qquad (I)$$

wherein $R^1, R^2$, and $R^3$ independently represent a hydrogen atom or a $C_1$ to $C_{10}$ hydrocarbon group, which may be substituted with at least one halogen atom, provided that $R^1$, $R^2$ and $R^3$ are not simultaneously hydrogen atoms, $R^4$, $R^5$ and $R^6$ independently represent a hydrogen atom or a $C_1$ to $C_{10}$ hydrocarbon group, which may be substituted with at least one halogen atom, a is an integer of 1 or more, b is an integer of 1 or more, c is 2, provided that $3 \leq a + b + c \leq 10000$, and the compound has at least one Si—H group.

7. A silicone-treated hydrophobic powder as claimed in claim 6, wherein, when an average particle size of the starting powder is not more than 0.1 μm, the silicone compound coated powder is heated in the second step at a temperature of 260 to 320° C. for 1 to 5 hours.

8. A silicone-treated hydrophobic powder as claimed in claim 6, wherein, when an average particle size of the starting powder is more than 0.1 μm, the silicone compound coated powder is heated in the second step at a temperature of 330 to 480° C. for 1 to 5 hours.

* * * * *

UNITED STATES PATENT AND TRADEMARK OFFICE
CERTIFICATE OF CORRECTION

PATENT NO. : 7,449,193 B2
APPLICATION NO. : 10/679298
DATED : November 11, 2008
INVENTOR(S) : Kanemaru et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 157 days.

Signed and Sealed this
First Day of March, 2011

David J. Kappos
*Director of the United States Patent and Trademark Office*